(12) United States Patent
Verban, Jr.

(10) Patent No.: US 7,866,979 B2
(45) Date of Patent: Jan. 11, 2011

(54) DENTAL DRILL SYSTEM AND STOP COLLAR FOR PREPARING IMPLANT BED FOR IMPLANTS

(76) Inventor: Emil M. Verban, Jr., 2103 E. Washington, Bloomington, IL (US) 61701

( * ) Notice: Subject to any disclaimer, the term of this patent is extended or adjusted under 35 U.S.C. 154(b) by 14 days.

(21) Appl. No.: 11/116,986

(22) Filed: Apr. 28, 2005

(65) Prior Publication Data

US 2006/0188840 A1 Aug. 24, 2006

Related U.S. Application Data

(60) Provisional application No. 60/656,639, filed on Feb. 24, 2005.

(51) Int. Cl.
*A61C 3/00* (2006.01)
(52) U.S. Cl. ........................................................ 433/75
(58) Field of Classification Search ................... 433/72, 433/75, 76, 165; 408/202, 14; 606/80, 172, 606/79, 96
See application file for complete search history.

(56) References Cited

U.S. PATENT DOCUMENTS

| | | | | |
|---|---|---|---|---|
| 5,078,552 A | * | 1/1992 | Albel | 408/1 R |
| 6,514,258 B1 | * | 2/2003 | Brown et al. | 606/80 |
| 6,739,872 B1 | * | 5/2004 | Turri | 433/75 |
| 2006/0008332 A1 | * | 1/2006 | Greenberg et al. | 408/202 |
| 2006/0257220 A1 | * | 11/2006 | Gertner | 408/202 |

\* cited by examiner

*Primary Examiner*—Cris L Rodriguez
*Assistant Examiner*—Sunil K Singh
(74) *Attorney, Agent, or Firm*—McDonnell Boehnen Hulbert & Berghoff LLP

(57) ABSTRACT

A dental drill system and method for drilling a socket to a predetermined depth and diameter which is sized to receive an implant includes a first drill bit with a first bit diameter, a second drill bit with a second bit diameter, wherein the second bit diameter is greater than the first bit diameter. A stop collar is provided which includes a body with a first bore formed through the body. The first bore is adapted to receive the first drill bit. A second bore is formed coaxial with the first bore and extends a portion less than an entire length of the body, wherein the second bore is greater than the first bore and adapted to receive the second drill bit.

12 Claims, 2 Drawing Sheets

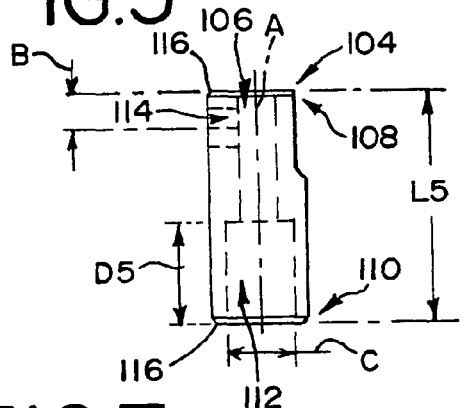
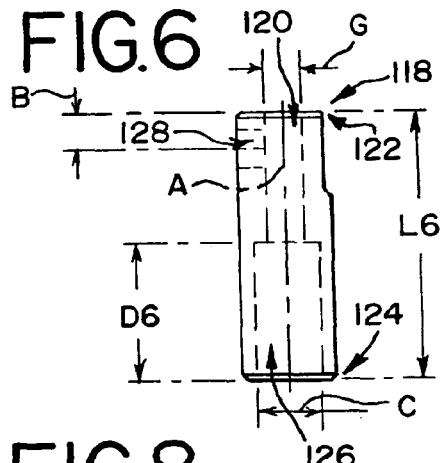
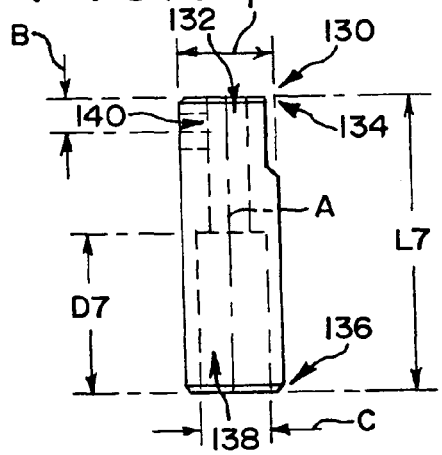
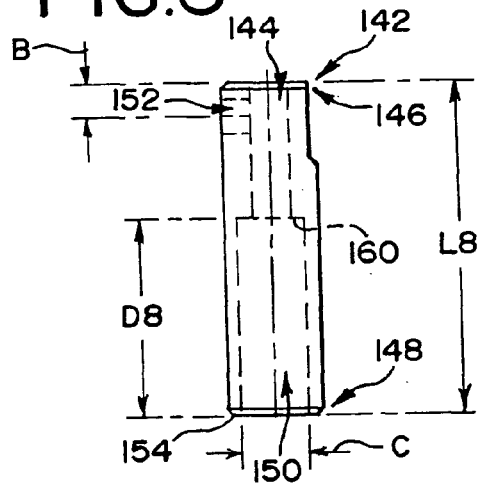
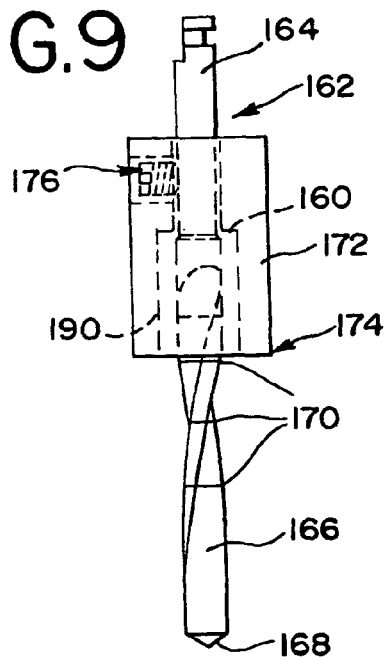
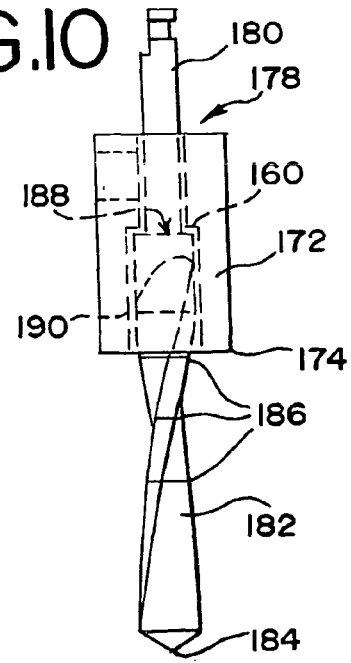

DENTAL DRILL SYSTEM AND STOP COLLAR FOR PREPARING IMPLANT BED FOR IMPLANTS

This application claims the benefit of U.S. Provisional Application No. 60/656,639, filed Feb. 24, 2005.

FIELD OF THE INVENTION

The invention relates to the field of Dentistry and more particularly, to drills and the use of drills in the field of Dentistry. Specifically, the invention relates to drills and a drill stop for use in preparing a site, e.g., an implant bed or socket for receiving a dental implant. The drill stop is sized and shaped to use with more than one size of drill bit and is configured to both provide a reference to judge the angle of drilling and assure proper depth of drilling.

BACKGROUND OF THE INVENTION

Use of endosseous dental implants for the foundation for various dental restorations, like bridges, crowns, dentures and the like is well known in the art. Positioning of the dental implant is absolutely critical. For many well known reasons, long term success of the implant, and ultimately of the restoration, hinges on drilling a correct placement, diameter, depth and alignment of a socket or the like for receiving the implant. It will be appreciated that this necessitates careful planning as well as careful formation of the socket.

A conventional and well known method of implanting solid screw implants will be briefly reviewed to provide some background regarding the need for and process of careful preparation of the implant bed. A first step of the procedure involves exposing the bone ridge and preparation of the implant bed for receiving the implant or implants. The ridge is flattened as necessary with a relatively large bur, e.g. a Ø3.1 mm (3.1 mm diameter) round bur at a maximum of 800 R.P.M. (revolutions per minute). The flattened site may be marked with a small round bur (Ø1.4 mm) at the center of the intended bore for the hole or socket in which the implant is to be positioned.

After preparation of the site, a pilot hole is formed at the implant site with a pilot drill bit (Ø2.2 mm) is inserted to a depth equal to or slightly deeper than the insertion depth of the implant, for example approximately 6.0 mm for a 6 mm implant. Slight pressure should be used during drilling with sufficient cooling throughout the entire sequence.

The depth and alignment of the resulting pilot hole is checked with a Ø2.2 mm alignment pin. Both angle and depth of the pilot hole must be precise and since the operation is taking part in the patient mouth, it can be seen that there is an inherent difficulty with this technique, namely, both alignment and depth cannot be accurately gauged at the same time. Fortunately, an unsatisfactory implant axis can still be corrected at this step in the procedure. After the alignment of the pilot hole is checked and, if necessary, corrected, drilling continues with the Ø2.2 mm drill bit to the depth of the implant selected or slightly deeper and the depth is again checked with the Ø2.2 mm alignment pin. A Ø2.8 mm drill bit, also known in the industry as a pilot bit, may be used to widen the pilot hole to the appropriate depth. The depth is again checked with a Ø2.2/2.8 mm depth gauge.

If an Ø3.0 mm reduced diameter or narrow neck implant is being placed, the next step would be to tap the site and insert the implant. If not, a Ø3.5 mm twist drill bit is used to widen the initial hole to the appropriate depth. The depth is measured with a Ø3.5 mm depth gauge. If an Ø4.1 mm standard diameter implant is being placed, the next step would be to tap the site and insert the implant. If not, a Ø4.2 mm twist drill bit is used and the depth is checked with a Ø4.2 mm depth gauge. The site can then be tapped and an Ø4.8 mm wide diameter or wide neck implant may be inserted. It will be understood that the example given herein is illustrative and not limiting in nature. In general, to summarize, the preparation process includes drilling a pilot hole at the implant site at the correct position and angle and then widening the hole with at least a second sized drill to the correct width and depth to receive the implant. The second drill may also be a counterbore type drill in some instances. Further widening of the hole or socket is performed to accommodate a predetermined width and length of implant.

Each implant or post must form a solid, enduring base with sufficient stability to withstand the tremendous mechanical pressure involved in normal chewing, so typically three to six months are allowed for the implant to incorporate into or bond to the bone. During the wait, a temporary bridge or denture is provided to the patient to facilitate eating and to maintain facial muscle support; meanwhile, a lab custom designs and manufactures the restoration to be placed over the implant top(s).

Once the implant post has bonded with the jawbone, and the artificial teeth are ready, the final step of the implant placement process involves placing the prepared restoration (s) over the protruding implant post(s). This results in a secure, attractive, replacement tooth or set of teeth, designed to function as effectively as one's natural teeth. Depending on the number of teeth involved, this final part of the implant process requires only a short time to complete.

Since it is critical to accurately position and angle the socket and since it is critical to prepare the depth of the socket accurately, it can be seen that gauging the angle and depth by eye during drilling can be difficult indeed. Thus, there is a demand for a method and device to accurately prepare a socket for receiving a dental implant. The present invention satisfies the demand.

SUMMARY OF THE INVENTION

Now, with the foregoing in mind, the current invention includes aspects directed to a stop collar for use with one or more drill bit, including a body with an axial bore formed through the body. The axial bore has a first diameter. A counterbore is formed coaxial with the axial bore and extends a portion of a length of the body. The counterbore includes a second diameter, wherein the second diameter is greater than the axial bore.

Another aspect of the invention builds upon the foregoing by providing a dental drill system for drilling a socket to a predetermined depth and diameter which is sized to receive an implant and includes a first drill bit including a first bit diameter, a second drill bit including a second bit diameter wherein the second bit diameter is greater than the first bit diameter. A stop collar is provided which includes a body, wherein the stop collar includes a first bore formed through the body. The first bore is adapted to receive the first drill bit. A second bore is formed coaxial with the first bore and extends a portion less than an entire length of the body, wherein the second bore is greater than the first bore and adapted to receive the second drill bit.

Yet another aspect of the invention provides a method of drilling a socket to a predetermined depth and width for placement of a dental implant therein and includes the steps of providing a pilot drill bit including a body portion including a first body diameter. A second drill bit is provided with a body portion including a second body diameter corresponding to the predetermined width, wherein the second body diameter is greater than the first body diameter. A stop collar is provided with a central bore formed along an axial length of the stop collar, wherein the central bore is sized to receive the first body diameter but not the second body diameter and a counterbore formed in a bottom end of the stop collar, wherein the counterbore is sized to receive the second body diameter. The stop collar is positioned on the pilot drill bit with a predetermined distance between the bottom of the stop collar and a point of the pilot drill, the predetermined distance corresponding to the predetermined depth. A pilot hole is drilled a depth equal to the predetermined depth. The stop collar is positioned on the second drill bit at about the predetermined distance. The socket is positioned at the predetermined depth by stopping the socket drilling at the predetermined depth with the stop collar.

The present invention, in perhaps one of its broadest expressions, includes a stop collar which adapted to be both selectively positionable on a variety of sizes of drill bits and provides an accurate gauge for drilling depth as well as angle of penetration.

The present invention will be further appreciated, and its attributes and advantages further understood, upon consideration of the following detailed description of an embodiment of the invention, taken in conjunction with the accompanying drawings.

BRIEF DESCRIPTION OF THE DRAWINGS

FIG. 5 shows a "long" drill sleeve in a side cross-sectional view according to a fifth embodiment of the present invention.

FIG. 6 shows a "long" drill sleeve in a side cross-sectional view according to a sixth embodiment of the present invention.

FIG. 7 shows a "long" drill sleeve in a side cross-sectional view according to a seventh embodiment of the present invention.

FIG. 8 shows a "long" drill sleeve in a side cross-sectional view according to an eighth embodiment of the present invention.

FIG. 9 shows an example of a twist drill used for forming a pilot hole.

FIG. 10 shows an example of a second twist drill for forming a final bore for a socket to receive an implant.

DETAILED DESCRIPTION OF EMBODIMENTS OF THE INVENTION

The embodiments of the invention described hereinafter have been particularly adapted for use in the field of Dentistry. However, it will be understood that other fields may be contemplated by the present invention.

As a preliminary matter, the stop collars shown in FIGS. 1-4 are sized for use with short shank pilot, twist or fluted drill bits and the collars shown in FIGS. 5-8 are sized for use with long shank pilot, twist or fluted drill bits. It should also be noted that the method of forming a pilot hole followed by forming the socket with increasing diameter drill bits proceeds along the same stepwise enlargement of the socket as described above with the additional benefit of a drill bit stop collar according to the present invention. For example, an embodiment of the invention involves first drill a pilot hole using a 2.2 mm pilot drill bit followed by a 2.8 mm drill bit. At this stage a 3.3 mm implant may be inserted into the socket. If a 4.1 mm implant is to be used, the 2.8 mm drill bit is followed by a 3.5 twist drill. If a 4.8 mm implant is to be used, the 3.5 twist drill is followed by a 4.2 mm twist drill.

Figure 1:
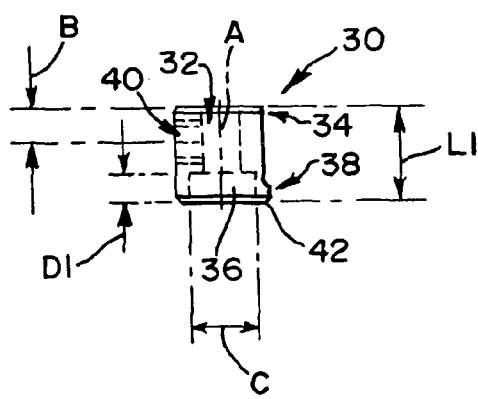
FIG. 1 shows a "short" style drill sleeve in a side cross-sectional view according to an embodiment of the present invention.

Referring to the drawings, FIG. 1 shows a drill bit stop collar 30 according to an embodiment of the invention configured to produce a 14 mm deep socket with a short shank drill bit. The stop collar 30 includes a generally outer cylindrical shape having an axial length (L1) of 5.37 mm. Preferably, the stop collar 30 is formed of 304 stainless steel, but it will be appreciated that any number of materials may be used such as other types of stainless steel, steel, aluminum, and titanium, alloys of various metals and/or materials, ceramics, plastic materials, combinations thereof, composites or any other suitable material. All other examples of stop collars shown herein may be made of the same or an equivalent material or combination of materials. Furthermore, it will be appreciated that a number of outer shapes and sized may be suitable so long as it is usable in the mouth and does not interfere with the drilling process as will be explained in more detail below.

The longitudinal axis of the stop collar 30 is indicated at A along the long axis of the collar. The stop collar 30 has an axial bore 32 extending along the length L1 from a first or proximal end 34 of the collar and centered on axis A to a second or distal end 38. The axial bore 32 has a diameter of 2.33 mm. An axial counterbore 36 is centered on the axis A and extends inwardly from the second end 38 of the collar 30. The counterbore 36 has a depth D1 of 1.65 mm from the second end 38 and a diameter C of 4.21 mm.

A set screw opening 40 is formed through the wall or side of the collar 30 and extends in communication with the axial bore 32. The center of the set screw opening 40 is indicated at B, which is a distance of 2.04 mm from the first end 34. The set screw opening 40 is tapped to receive a set screw (not shown) for securing the collar 30 to a drill bit, i.e., the shaft or shank thereof (see FIG. 9. Preferably, the axis of the set screw opening 40 is normal to axis A. Preferably, the set screw (not shown) includes a hex drive socket drivable by a ball end wrench or the like to provide functionality at up to about 25 degrees.

The ends 34, 38 of collar 30 preferably include a chamfer 42, which in the preferred embodiment has a width of 0.03 mm. Of course, it will be understood that the chamfer may be other suitable widths or a curved radius to prevent the ends 34, 38 of the collar 30 from causing any injury or damage.

Figure 2:
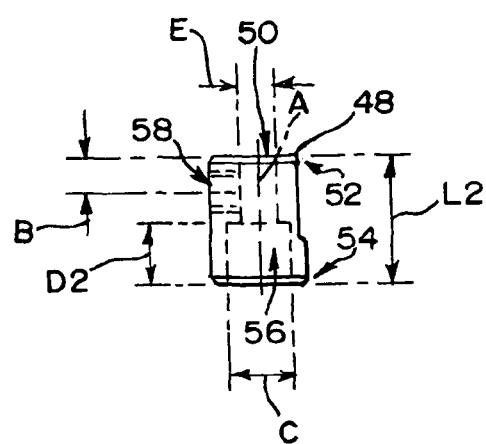
FIG. 2 shows a "short" drill sleeve in a side cross-sectional view according to a second embodiment of the present invention.

FIG. 2 shows a drill bit stop collar 48 according to another embodiment of the invention. The drill bit stop collar 48 is configured to produce a 12 mm deep socket with a short shank drill bit. The stop collar 48 is a generally cylindrical shape having an axial length (L2) of 7.22 mm. Preferably, the stop collar is formed of stainless steel as detailed above, but it will be appreciated that any number of suitable materials may be used. The stop collar 48 axis is indicated at A along the long axis of the collar. The stop collar 48 has an axial bore 50 extending along length L2 from a first end 52 of the collar, centered on axis A, to a second end 54. The axial bore 50 has a diameter E of 2.33 mm.

An axial counterbore 56 is centered on the axis A and extends inwardly from the second end 54 of the collar 48. The counterbore 56 has a depth D2 of 3.55 mm from the second end 54 and a diameter C of 4.21 mm.

A set screw opening 58 is formed through the side of the collar 48 and in communication with the axial bore 50. The center of the set screw opening 58 is indicated at distance B and is centered at a distance of 2.04 mm from the first end 52. The set screw opening 58 is tapped to receive a set screw (not shown) for securing the collar 50 to a drill bit, or the shaft or shank thereof (not shown). Preferably, the axis of the set screw opening 58 is normal to axis A.

Figure 3:
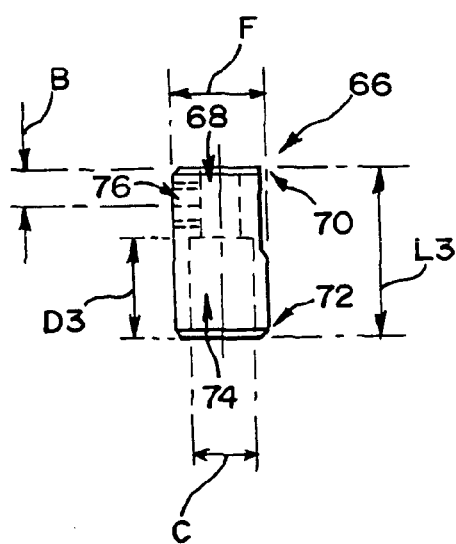
FIG. 3 shows a "short" drill sleeve in a side cross-sectional view according to a third embodiment of the present invention.

FIG. 3 shows a drill bit stop collar 66 according to another embodiment of the invention. The drill bit stop collar 66 is configured to produce a 10 mm deep socket with a short shank drill bit. The stop collar 66 is a generally cylindrical shape having an axial length (L3) of 9.23 mm and a radial diameter of 5.54 mm indicated at F. Preferably, the stop collar 66 is formed of stainless steel as detailed above, but it will be appreciated that any number of suitable materials may be used. The stop collar 66 axis is indicated at A along the long axis of the collar. The stop collar 66 has an axial bore 68 extending along length L3 from a first end 70 of the collar, centered on axis A, to a second end 72. The axial bore 68 has a diameter of 2.33 mm.

An axial counterbore 74 is centered on the axis A and extends inwardly from the second end 72 of the collar 66. The counterbore 74 has a depth D3 of 5.41 mm from the second end 72 and a diameter C of 4.21 mm.

A set screw opening 76 is formed through the side of the collar 66 and in communication with the axial bore 68. The center of the set screw opening 76 is indicated at distance B and is centered at a distance of 2.04 mm from the first end 70. The set screw opening 76 is tapped to receive a set screw (not shown) for securing the collar 66 to a drill bit, or the shaft or shank thereof (not shown). Preferably, the axis of the set screw opening 76 is normal to axis A.

Figure 4:
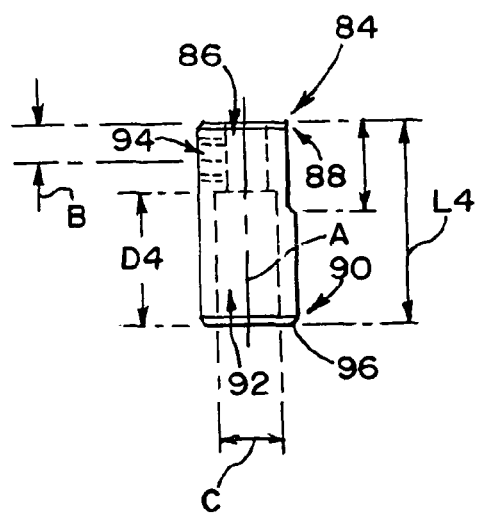
FIG. 4 shows a "short" drill sleeve in a side cross-sectional view according to a fourth embodiment of the present invention.

FIG. 4 shows a drill bit stop collar 84 according to another embodiment of the invention. The drill bit stop collar 84 is configured to produce an 8 mm deep socket with a short shank drill bit. The stop collar 84 is a generally cylindrical shape having an axial length (L4) of 11.23 mm and a radial diameter of 5.54 mm. Preferably, the stop collar 84 is formed of stainless steel as detailed above, but it will be appreciated that any number of suitable materials may be used. The stop collar 84 axis is indicated at A along the long axis of the collar. The stop collar 84 has an axial bore 86 extending along length L4 from a first end 88 of the collar, centered on axis A, to a second end 90. The axial bore 86 has a diameter of 2.33 mm.

An axial counterbore 92 is centered on the axis A and extends inwardly from the second end 90 of the collar 84. The counterbore 92 has a depth D4 of 7.41 mm from the second end 90 and a diameter C of 4.21 mm.

A set screw opening 94 is formed through the side of the collar 84 and in communication with the axial bore 86. The center of the set screw opening 94 is indicated at distance B and is centered at a distance of 2.04 mm from the first end 88. The set screw opening 94 is tapped to receive a set screw (not shown) for securing the collar 84 to a drill bit, or the shaft or shank thereof (not shown). Preferably, the axis of the set screw opening 94 is normal to axis A. A chamfer of 0.03 mm is shown at 96.

FIGS. 5-8 are different from the foregoing set of collars by having a greater overall axial length to be used with a drill bit having a long shank.

FIG. 5 shows a drill bit stop collar 104 according to another embodiment of the invention. The drill bit stop collar 104 according to an embodiment of the invention configured to produce a 14 mm deep socket with a long shank drill bit. The stop collar 104 is a generally cylindrical shape having an axial length L5 of 13.58 mm and a radial diameter of 5.54 mm. Preferably, the stop collar 104 is formed of stainless steel as detailed above, but it will be appreciated that any number of suitable materials may be used. The stop collar 104 axis is indicated at A along the long axis of the collar. The stop collar 104 has an axial bore 106 extending along length L5 from a first end 108 of the collar, centered on axis A, to a second end 110. The axial bore 106 has a diameter of 2.33 mm.

An axial counterbore 112 is also centered on the axis A and extends inwardly from the second end 110 of the collar 104. The counterbore 112 has a depth D5 of 6.06 mm from the second end 110 and a diameter C of 4.21 mm.

A set screw opening 114 is formed through the side of the collar 104 and in communication with the axial bore 106. The center of the set screw opening 114 is indicated at distance B and is centered at a distance of 2.03 mm from the first end 108. The set screw opening 114 is tapped to receive a set screw (not shown) for securing the collar 104 to a drill bit, or the shaft or shank thereof (not shown). Preferably, the axis of the set screw opening 114 is normal to axis A.

The ends 108, 110 of collar 104 preferably include a chamfer 116, which in the preferred embodiment has a width of 0.03 mm. Of course, it will be understood that the chamfer may be other suitable widths.

FIG. 6 shows a drill bit stop collar 118 according to another embodiment of the invention. The drill bit stop collar 118 is configured to produce a 12 mm deep socket with a long shank drill bit.

The stop collar 118 is a generally cylindrical shape having an axial length L5 of 15.49 mm. Preferably, the stop collar is formed of stainless steel as detailed above, but it will be appreciated that any number of suitable materials may be used. The stop collar 118 axis is indicated at A along the long axis of the collar. The stop collar 118 has an axial bore 120 extending along length L6 from a first end 122 of the collar, centered on axis A, to a second end 124. The axial bore 120 has a diameter of 2.33 mm shown at G.

An axial counterbore 126 is centered on the axis A and extends inwardly from the second end 124 of the collar 118. The counterbore 126 has a depth D6 of 8.06 mm from the second end 124 and a diameter C of 4.21 mm.

A set screw opening 128 is formed through the side of the collar 118 and in communication with the axial bore 120. The center of the set screw opening 128 is indicated at distance B and is centered at a distance of 2.03 mm from the first end 122. The set screw opening 128 is tapped to receive a set screw (not shown) for securing the collar 118 to a drill bit, or the shaft or shank thereof (not shown). Preferably, the axis of the set screw opening 128 is normal to axis A.

FIG. 7 shows a drill bit stop collar 130 according to another embodiment of the invention. FIG. 7 shows a drill bit stop collar 130 according to an embodiment of the invention configured to produce a 10 mm deep socket with a long shank drill bit. The stop collar 130 is a generally cylindrical shape having an axial length (L7) of 17.58 mm and a radial diameter of 5.54 mm indicated at F. Preferably, the stop collar 130 is formed of stainless steel as detailed above, but it will be appreciated that any number of suitable materials may be used. The stop collar 130 axis is indicated at A along the long axis of the collar. The stop collar 130 has an axial bore 132 extending along length L7 from a first end 134 of the collar, centered on axis A, to a second end 136. The axial bore 132 has a diameter of 2.33 mm.

An axial counterbore 138 is centered on axis A and extends inwardly from the second end 136 of the collar 130. The counterbore 138 has a depth D7 of 9.55 mm from the second end 136 and a diameter C of 4.21 mm.

A set screw opening 140 is formed through the side of the collar 130 and in communication with the axial bore 132. The center of the set screw opening 140 is indicated at distance B and is centered at a distance of 2.03 mm from the first end 134. The set screw opening 140 is tapped to receive a set screw (not shown) for securing the collar 130 to a drill bit, or the shaft or shank thereof (not shown). Preferably, the axis of the set screw opening 140 is normal to axis A.

FIG. 8 shows a drill bit stop collar 142 according to another embodiment of the invention. FIG. 8 shows a drill bit stop collar 142 configured to produce a 8 mm deep socket with a long shank drill bit. The stop collar 142 is a generally cylindrical shape having an axial length (L8) of 19.58 mm and a radial diameter of 5.54 mm. Preferably, the stop collar 142 is formed of stainless steel as detailed above, but it will be appreciated that any number of suitable materials may be used. The stop collar 142 axis is indicated at A along the long axis of the collar. The stop collar 142 has an axial bore 144 extending along length L8 from a first end 146 of the collar, centered on axis A, to a second end 148. The second end 148 of collar 142 preferably includes a chamfer 154. The axial bore 144 has a diameter of 2.33 mm.

An axial counterbore 150 is centered on the axis A and extends inwardly from the second end 148 of the collar 142. The counterbore 150 has a depth D8 of 11.55 mm from the second end 148 and a diameter C of 4.21 mm.

A set screw opening 152 is formed through the side of the collar 142 in communication with the axial bore 144. The center of the set screw opening 152 is indicated at distance B and is centered at a distance of 2.03 mm from the first end 146. The set screw opening 152 is tapped to receive a set screw (not shown) for securing the collar 142 to a drill bit, or the shaft or shank thereof (not shown). Preferably, the axis of the set screw opening 152 is normal to axis A.

All of the collars shown in FIGS. 1-4 and the collars shown in FIGS. 5-8 have common bore and counterbore diameters. Of course, it will be understood that the examples shown in FIGS. 1-8 are designed to be used with a specific set of drill bits and may be adapted for other sets of drill bits by adjusting the specifications accordingly.

Each of the collars shown in FIGS. 1-8 include a shoulder 160 formed between a respective counterbore and bore (see FIG. 9 for example). The shoulder contacts or indexes to a respective wide part (see FIG. 10) of a drill bit and automatically forms the depth stop function of the collar thereby. Furthermore, when connected to a drill bit a lower edge of the collar provides a sight line by which the user may accurately gauge the angle of the drill bit and the socket being formed as will be explained below in more detail.

FIG. 9 shows a twist drill bit of a pilot bit type 162. Main parts of the bit 162 include the shank or shaft 164, which is inserted into a drill (not shown), the body 166 and point 168. The body 166 of the bit 162 includes marks 170 which correspond to predetermined depths from the point 168 of the bit. A collar 172 is shown in position on the bit 162 and having a bottom edge 174 aligned with a third of the marks 170. It can be seen that the collar 172 can be positioned on the bit by inserting the bit 162 from either the bottom or top of the collar. The collar 172 is secured in place by tightening a set screw 176 against the shaft 164. The positioning of the collar 172 on the bit 162 is done during this step by aligning the bottom 174 with the mark 170 at the appropriate predetermined depth corresponding to the specification of the implant (not shown) which will be used. In the next step, discussed more fully below, the collar 172 automatically indexes to the bit in the desired position to provide correct drilling depth.

FIG. 10 shows a second bit 178 having a shaft 180, body 182 and point 184 opposite the shaft. The width of the bit 178 is sized to provide an appropriate diameter hole or socket to receive a predetermined implant. Typically, the diameter of the bit is slightly less (e.g., 0.5 mm) than the implant so that outer threads of the implant positively engage the walls of the socket and, in time, forms a secure attachment with the bone. The shoulder 160 of the collar 172 engages with a transition portion 188 of the bit 178 where the diameter of the bit widens, i.e. where the diameter of the shaft 180 widens to the diameter of the body 182. This way the bottom 174 collar 172 aligns to the same depth of penetration denoted by mark 186 as compared to mark 170 of the first bit 162.

In use, and referring to FIGS. 9 and 10, the first bit or pilot bit 162 is fit with collar 172 at an appropriate depth setting by aligning the bottom 174 of the collar with an appropriate mark 170 of the bit. The collar 172 is secured to the shaft 164 of the bit with set screw 176. The user forms the socket by drilling at the correct angle using the bottom 174 of the collar 172 as a gauge. When the collar 172 is flush with the prepared site the pilot bit is removed. The user then positions the same collar 172 on the next size bit 178, and lowers the collar over the shaft 180 until contact is made between portion 188 and shoulder 160. The bottom 174 of the collar 172 should be aligned with the same mark 186 at the same depth from the point 184 as that of the pilot bit 162. Drilling resumes with the larger diameter bit 178 (regardless of whether it is the final diameter bit) until the collar 172 is flush with the prepared site. If a larger bore socket is needed, drilling continues with larger diameter bits. The counterbore 190 of the collar 172 is sized to accommodate the diameter of each bit.

While the present invention has been described with respect to a particular embodiment, those of skill in this art will recognize even more variations, applications and modifications which will still fall within the spirit and scope of the invention, all as intended to come within the ambit and reach of the following claims.

What is claimed is:

1. A dental drill system for use in drilling at a drilling site on a patient for placement of a dental implant, the dental drill system comprising:

a first drill bit having a shaft and a drill-bit body, the drill-bit body having a point at an operative end thereof, the drill-bit body further having a mark at a predetermined distance from the point;

a second drill bit having a shaft and a drill-bit body, the drill-bit body having a point at an operative end thereof, wherein the second drill bit has a transition portion between the shaft and the drill-bit body, the drill-bit body having a diameter greater than that of the shaft; and a stop collar comprising:

a stop-collar body having an axial stop-collar body length extending from a first end of the stop-collar body to a second end of the stop-collar body, wherein, in operation, the stop collar is generally oriented such that a longitudinal axis of the stop-collar body is substantially normal to a drilling site on a patient, such that the second end of the stop-collar body is closer than the first end of the stop-collar body to the drilling site, an axial bore extending through the stop-collar body, wherein the axial bore extends the entire axial body length from the first end of the stop-collar body to the second end of the stop-collar body, coaxial with the longitudinal axis of the stop-collar body, wherein the axial bore has an axial-bore diameter, wherein the stop collar comprises securing means for securing the first drill bit in the axial bore such that the drill-bit body of the first drill bit extends the predetermined distance beyond the second end of the stop-collar body when the first drill bit is secured by the securing means such that the mark on the drill-bit body of the first drill bit is aligned with the second end of the stop-collar body, wherein the drill-bit body of the first drill bit has a diameter that is less than or equal to the axial-bore diameter, and an axial counterbore extending partially through the stop-collar body, wherein the axial counterbore is coaxial with the axial bore and has an axial-counterbore diameter that is greater than the axial-bore diameter, wherein the axial counterbore extends inwards through the stop-collar body from the second end of the stop-collar body such that (1) a first end of the axial counterbore is co-located with the second end of the stop-collar body and (2) a second end of the axial counterbore forms a shoulder portion of the stop-collar body between the axial bore and the axial counterbore, wherein the drill-bit body of the second drill bit extends the predetermined distance beyond the second end of the stop-collar body when the transition portion of the second drill bit contacts the shoulder portion and when the second drill bit is secured by the securing means, wherein the drill-bit body of the second drill bit has a diameter greater than the axial-bore diameter, wherein the predetermined distance corresponds to a depth specification for a dental implant for the drilling site, and wherein the diameter of the drill-bit body of the second drill bit corresponds to a diameter specification for the dental implant.

2. The dental drill system of claim 1, further comprising one or more intermediate drill bits, each having a shaft, a drill-bit body having a point at an operative end thereof, and a transition portion between its respective shaft and drill-bit body, the drill-bit body of each intermediate drill bit having a diameter greater than the axial-bore diameter and less than the axial-counterbore diameter, the drill-bit body of each intermediate drill bit extending the predetermined distance beyond the second end of the stop-collar body when its respective transition portion contacts the shoulder portion of the stop collar and when the intermediate drill bit is secured by the securing means.

3. The dental drill system of claim 1, wherein the stop collar has a generally cylindrical shape.

4. The dental drill system of claim 1, wherein the stop collar is formed of stainless steel.

5. The dental drill system of claim 1, wherein the securing means comprises a set screw.

6. The dental drill system of claim 1, wherein the diameter of the drill-bit body of the second drill bit corresponding to the diameter specification for the dental implant comprises the diameter of the drill-bit body of the second drill bit being slightly less than a diameter of the dental implant.

7. A method for drilling at a drilling site on a patient for placement of a dental implant, the method comprising:
providing a first drill bit having a shaft and a drill-bit body, the drill-bit body having a point at an operative end thereof, the drill-bit body further having a mark at a predetermined distance from the point;

providing a second drill bit having a shaft and a drill-bit body, the drill-bit body having a point at an operative end thereof, wherein the second drill bit has a transition portion between the shaft and the drill-bit body, the drill-bit body having a diameter greater than that of the shaft;

providing a stop collar comprising:
a stop-collar body having an axial stop-collar body length extending from a first end of the stop-collar body to a second end of the stop-collar body, wherein, in operation, the stop collar is generally oriented such that a longitudinal axis of the stop-collar body is substantially normal to a drilling site on a patient, such that the second end of the stop-collar body is closer than the first end of the stop-collar body to the drilling site, an axial bore extending through the stop-collar body, wherein the axial bore extends the entire axial body length from the first end of the stop-collar body to the second end of the stop-collar body, coaxial with the longitudinal axis of the stop-collar body, wherein the axial bore has an axial-bore diameter, wherein the stop collar comprises securing means for securing the first drill bit in the axial bore, wherein the drill-bit body of the first drill bit has a diameter that is less than or equal to the axial-bore diameter, and an axial counterbore extending partially through the stop-collar body, wherein the axial counterbore is coaxial with the axial bore and has an axial-counterbore diameter that is greater than the axial-bore diameter, wherein the axial counterbore extends inwards through the stop-collar body from the second end of the stop-collar body such that (1) a first end of the axial counterbore is co-located with the second end of the stop-collar body and (2) a second end of the axial counterbore forms a shoulder portion of the stop-collar body between the axial bore and the axial counterbore, wherein the drill-bit body of the second drill bit extends the predetermined distance beyond the second end of the stop-collar body when the transition portion of the second drill bit contacts the shoulder portion, wherein the drill-bit body of the second drill bit has a diameter greater than the axial-bore diameter, wherein the predetermined distance corresponds to a depth specification for a dental implant for the drilling site, and wherein the diameter of the drill-bit body of the second drill bit corresponds to a diameter specification for the dental implant;

securing the stop collar to the first drill bit using the securing means, such that the mark on the drill-bit body of the first drill bit is aligned with the second end of the stop-collar body, resulting in the drill-bit body of the first drill bit extending the predetermined distance beyond the second end of the stop-collar body;

after so securing the stop collar to the first drill bit, drilling a pilot hole at the drilling site to a depth equal to the predetermined distance, wherein drilling the pilot hole comprises drilling until the second end of the stop collar contacts the drilling site with the point of the first drill bit at the depth equal to the predetermined distance;

positioning the stop collar on the second drill bit, wherein positioning the stop collar on the second drill bit comprises placing the transition portion of the second drill bit in contact with the shoulder portion of the stop collar and securing the second drill bit using the securing means; and widening the pilot hole to approximately the diameter of the drill body of the second drill bit by drilling into the pilot hole with the second drill bit having the stop collar positioned thereon, until the second end of the stop collar contacts the drilling site with the point of the second drill bit at the depth equal to the predetermined distance.

8. The method of claim 7, further comprising intermediately widening the pilot hole by drilling at the drilling site with the stop collar positioned on one or more intermediate drill bits, each having a shaft, a drill-bit body having a point at an operative end thereof, and a transition portion between its respective shaft and drill-bit body, the drill-bit body of each intermediate drill bit having a diameter greater than the axial-bore diameter and less than the axial-counterbore diameter, the drill-bit body of each intermediate drill bit extending the predetermined distance beyond the second end of the stop-collar body when its respective transition portion contacts the shoulder portion of the stop collar and the intermediate drill bit is secured using the securing means.

9. The method of claim 7, wherein the stop collar has a generally cylindrical shape.

10. The method of claim 7, wherein the stop collar is formed of stainless steel.

11. The method of claim 7, wherein the securing means comprises a set screw.

12. The method of claim 7, wherein the diameter of the drill-bit body of the second drill bit corresponding to the diameter specification for the dental implant comprises the diameter of the drill-bit body of the second drill bit being slightly less than a diameter of the dental implant.

* * * * *